(12) United States Patent
Nakano et al.

(10) Patent No.: US 6,984,500 B2
(45) Date of Patent: Jan. 10, 2006

(54) METHOD FOR DETECTING MICROORGANISMS AND DETECTION KIT

(76) Inventors: Tomota Nakano, c/o Kanto Kagaku Kabushiki Kaisha Iseharakojo, 21, Suzukawa, Isehara-shi, Kanagawa (JP); Makoto Kurihara, c/o Kanto Kagaku Kabushiki Kaisha Iseharakojo, 21, Suzukawa, Isehara-shi, Kanagawa (JP)

( * ) Notice: Subject to any disclaimer, the term of this patent is extended or adjusted under 35 U.S.C. 154(b) by 302 days.

(21) Appl. No.: 10/215,670

(22) Filed: Aug. 9, 2002

(65) Prior Publication Data

US 2003/0068777 A1 Apr. 10, 2003

(30) Foreign Application Priority Data

Aug. 10, 2001 (JP) ............................. 2001-244586

(51) Int. Cl.
  *C12Q 1/04* (2006.01)
  *C12Q 1/18* (2006.01)
  *C12N 5/00* (2006.01)
  *G01N 33/53* (2006.01)

(52) U.S. Cl. ............................. 435/34; 435/32; 435/25; 435/404; 435/975

(58) Field of Classification Search ................. 435/32, 435/25, 29, 404, 975, 2, 9, 34
See application file for complete search history.

(56) References Cited

U.S. PATENT DOCUMENTS

| 5,498,528 A | 3/1996 | King ............................. 435/34 |
| 5,501,959 A | 3/1996 | Lancaster et al. ............. 435/32 |
| 5,523,214 A | 6/1996 | Horn ............................. 435/52 |
| 6,428,974 B1 * | 8/2002 | Nakano et al. ............... 435/32 |
| 2002/0022247 A1 | 2/2002 | Nakano et al. |
| 2003/0162164 A1 * | 8/2003 | Bochner et al. ............... 435/4 |

FOREIGN PATENT DOCUMENTS

| JP | 11-287796 | 4/1993 |
| JP | 07-107995 A | 10/1993 |
| WO | WO 96/28570 A1 | 9/1996 |
| WO | WO 99/32656 A1 | 7/1999 |

OTHER PUBLICATIONS

Webster's II New Riverside Dictionary (1994) (Houghton-Mifflin: Boston, MA) p. 667.*

Jahn et al. (1996) "Colorimetric Susceptibility Testing For *Aspergillus fumigatus*; Comparison of Menadione-Augmented 3-(4,5-Dimethyl-2-Thiazolyl)-2,5-Diphenyl-2H-Tetrazolium Bromide And Alamar Blue Tests," 34(8) *J. Clinical Microbiol.* 2039-2041.

Ishiyama et al. (1997) "A Highly Water-Soluble Disulfonated Tetrazolium Salt As A Chromogenic Indicator For NADH As Well As Cell Viability," 44 *Talanta* 1299-1305.

Matrai et al. (2000) "Invertase Production of Common Storage Moulds In Food And Feed Grains As A Possibility For Rapid Detection of *Aspergillus flavus* Group and *Aspergillus Fumigatus*," 61 *Intl. J. Food Microbiology* 187-191.

2000, 28 Journal of the Society for Antibacterial and Antifungal Agents Japan 601-609, with an abridged English translation.

Meletiadis et al. (2000) "Comparison of NCCLS and 3-(4, 5-Dimethyl-2-Thiazyl)-2,5-Diphenyl-2H-Tetrazolium Bromide (MTT) Methods of In Vitro Susceptibility Testing of Filamentous Fungi and Development of a New Simplified Method," 38(8) *J. Clin. Microbiol.* 2949-2954.

International J. of Food Microbiology, vol. 61, 2000, pp. 187-191.

WPI Accession No: 1988—019481 & SU 1313874 A (Sivolodskii).

GB Combined Search and Examination Report issued in connection with a counterpart GB Application No. GB 0217668.3.

* cited by examiner

*Primary Examiner*—Jean C. Witz
*Assistant Examiner*—Susan Hanley
(74) *Attorney, Agent, or Firm*—Keown & Associates; Wayne A. Keown; Joseph C. Zucchero

(57) ABSTRACT

A method for detecting a microorganism by coloration is provided that includes adding and reacting, in a liquid culture medium, an alkaline sensitizing solution and a coloring reagent containing a redox dye, the liquid culture medium having been inoculated with a test sample, thereby detecting the microorganism by coloration in the reaction. There is also provided a method for testing drug susceptibility of a microorganism using above-mentioned method. Furthermore, kits used in these methods are provided. The invention is useful to assess readily and objectively the growth of microorganism when carrying out e.g. a detection of microorganism in foods and a test such as a drug susceptibility test.

31 Claims, 2 Drawing Sheets

METHOD FOR DETECTING MICROORGANISMS AND DETECTION KIT

BACKGROUND OF THE INVENTION

The present invention relates to a method and a kit for detecting microorganisms in food and carrying out a test such as a drug susceptibility test for the purpose of selecting an optimal drug for treating a patient infected with a microorganism.

DESCRIPTION OF THE PRIOR ART

Fungi including yeast-like fungi and filamentous fungi are food spoilage pathogens and, in particular, the genus *Aspergillus* and the genus *Penicillium*, which are filamentous fungi, produce carcinogenic mycotoxins such as aflatoxin. They are also causative agents for profound mycosis, which has been an increasing problem in recent years. Detecting these fungi is therefore extremely important hygienically and medically.

Testing of these fungi is usually carried out by a culture method using an agar culture medium or a liquid culture medium, but since testing by the culture method takes 2 to 7 days, the length of time for the test is a problem. Furthermore, in the method using a liquid culture medium the degree of proliferation is mainly measured by employing a turbidity method in which the turbidity of the liquid culture is evaluated. Although this method is suitable for bacteria such as *E. coli*, it is not suitable for fungi and, in particular, fungi having poor dispersibility such as filamentous fungi, and the problem that precise measurement cannot be carried out has been identified.

In order to solve these problems, Matrai, et al., have directed attention toward invertase ($\beta$-D-fructofuranosidase) present in the genus *Aspergillus* and the genus *Penicillium*, and reported a method that enables a fungus to be detected in 20 to 48 hours by calorimetric analysis of glucose formed when the fungus is cultured in a culture medium containing sucrose (Matrai T., et al., Int. J. Food Microbiol., 61, 187–191, 2000). However, this method requires heating of the liquid culture during the evaluation, thereby complicating the operation.

Recently, rapid detection methods which employ various principles other than the culture method have been developed. In the food industry an ATP bioluminescence assay for environmental analysis and quality control has been employed accompanying the introduction of HACCP (Journal of the Society for Antibacterial and Antifungal Agents, Japan, 28, 601–609, 2000), and in the medical field use of a PCR assay has started ('Genetic Diagnosis of Mycosis', Medicalsense). However, the ATP assay has the problem that ATP derived from non-fungal material is detected and, in addition, a special image processor is required. The PCR assay has the problems of reaction inhibition due to contaminant components and the genes of dead fungi also being detected.

With regard to another method, there is a fluorescent staining method (Journal of the Society for Antibacterial and Antifungal Agents Japan, 28, 601–609, 2000), but since commercial devices are expensive, costing at least a few tens of millions of yen, the test cost becomes extremely high, which is a problem. Under such circumstances, there has been a strong desire for a low cost method that can detect microorganisms and, in particular, yeast-like fungi and filamentous fungi, specifically, quickly, and simply.

With regard to a method for testing the drug susceptibility of fungi, accompanying an increase in the onset frequency of profound mycosis and the emergence of strains exhibiting resistance to antifungal drugs, it has become essential to select an appropriate therapeutic drug for this infection, and there is therefore a desire to establish a simple and highly reliable test method based on a method for measuring the degree of fungal proliferation. In the United States, the National Committee for Clinical Laboratory Standards (NCCLS) has proposed in 1997 the 'Reference Method for Broth Dilution Antifungal Susceptibility Testing of yeasts; Approved Standard' (M27-A) as a method for testing the drug susceptibility of yeast-like fungi, and in 1998 the 'Reference Method for Broth Dilution Antifungal Susceptibility Testing of Conidium-Forming Filamentous Fungi; Proposed Standard' (hereinafter 'M38-P') as a method for testing the susceptibility of filamentous fungi. However, these methods require a long period of time before the test results are obtained, since the culture time may be 2 or 3 days depending on the type of fungus. Furthermore, since these methods all employ a turbidity method, they are not suitable for a fungus that proliferates in clump form, and there is a problem that it is difficult to decipher the fungal growth endpoint (80% fungal growth inhibition), particularly in the case of an azole antifungal. There is therefore a desire for a simpler and highly reproducible method for deciphering the fungal growth endpoint.

As means for solving these problems, various colorimetric methods for measuring the degree of fungal proliferation by colorimetry have been developed. Up to now, for example, a method using the tetrazolium salt 3-(4,5-dimethyl-2-thiazolyl)-2,5-diphenyl-2H-tetrazolium bromide (MTT), (Meletiadis J., J. Clin. Microbiol., 38, 2949–2954, 2000), a method using the redox indicator AlamarBlue™ (Alamar Biosciences Inc., Sacramento, Calif.) (Jahn B., J. Clin. Microbiol., 34, 2039–2041, 1996), and a vital staining method using Neutral Red (JP, 7-107995, A) have been reported. However, in the MTT method and the Neutral Red method the assessment operation is complicated, and the method using AlamarBlue™ has the problem that, depending on the strain, there are cases in which no fluorescence is produced, and the inhibitory concentration cannot be judged.

Nakano, et al., have reported a drug susceptibility test microplate in which a drug, a tetrazolium salt, 1-methoxy-5-methylphenazinium methylsulfate (1-methoxy PMS), potassium ferricyanide, and potassium ferrocyanide are made into a solid phase, and a method for testing drug susceptibility using same (JP, 11-287796, A). However, this microplate and the test method using it could only be applied to the measurement of yeast-like fungi, and the application thereof to filamentous fungi was difficult.

SUMMARY OF THE INVENTION

The present invention has therefore been carried out in view of the above-mentioned circumstances, and the object thereof is to provide a method for objectively assessing the proliferation of a microorganism and, in particular, the proliferation of a yeast-like fungus and a filamentous fungus by a simple operation in a short period of time when carrying out, for example, the detection of microorganisms in food and a test such as a drug susceptibility test for selecting an optimal drug for treating a patient infected with a microorganism; a drug susceptibility test method employing the above-mentioned method; and a kit used therein.

As a result of an intensive investigation by the present inventors in order to achieve the above-mentioned object, it has been found that the degree of proliferation of a microorganism, in particular, that of a yeast-like fungus and a filamentous fungus can be measured by colorimetry simply and in a short period of time by combining a coloring reagent containing, for example, a water-soluble tetrazolium salt such as WST-8 (2-(2-methoxy-4-nitrophenyl)-3-(4-nitrophenyl)-5-(2,4-disulfophenyl)-2H-tetrazolium, sodium salt: water soluble disulfonated tetrazolium salt, Ishiyama M., et al., Talanta, 44, 1299–1305, 1997) that decomposes to generate a formazan and then exhibits a color sensitively under alkaline conditions, with a liquid culture medium containing a non-reducing sugar such as sucrose. The present invention has thus been accomplished.

That is, the present invention relates to a method for detecting a microorganism, comprising adding and reacting, in a liquid culture medium, an alkaline sensitizing solution and a coloring reagent comprising a redox dye, the liquid culture medium having been inoculated with a test sample, thereby detecting the microorganism by coloration in the reaction.

Furthermore, the present invention relates to the above-mentioned detection method wherein the microorganism is a yeast-like fungus and/or a filamentous fungus.

Moreover, the present invention relates to the above-mentioned detection method wherein the liquid culture medium contains a non-reducing sugar.

Furthermore, the present invention relates to a kit for detecting a microorganism, comprising a liquid culture medium, an alkaline sensitizing solution, and a coloring reagent comprising a redox dye.

Moreover, the present invention relates to the above-mentioned detection kit wherein the redox dye is a water-soluble tetrazolium salt that forms a water-soluble formazan.

Furthermore, the present invention relates to the above-mentioned detection kit wherein the tetrazolium salt that forms the water-soluble formazan is 2-(2-methoxy-4-nitrophenyl)-3-(4-nitrophenyl)-5-(2,4-disulfophenyl)-2H-tetrazolium, sodium salt.

Moreover, the present invention relates to the above-mentioned detection kit wherein the coloring reagent further comprises an electron carrier, potassium ferricyanide, and potassium ferrocyanide.

Furthermore, the present invention relates to the above-mentioned detection kit wherein the electron carrier is 1-methoxy-5-methylphenazinium methylsulfate.

Moreover, the present invention relates to the above-mentioned detection kit wherein the liquid culture medium comprises a non-reducing sugar.

Furthermore, the present invention relates to the above-mentioned detection kit wherein the non-reducing sugar is sucrose.

Moreover, the present invention relates to the above-mentioned detection kit wherein the alkaline sensitizing solution is one that makes the pH of the liquid culture medium at least 9.

Furthermore, the present invention relates to the above-mentioned detection kit wherein the alkaline sensitizing solution is an aqueous solution of sodium hydroxide.

Moreover, the present invention relates to a method for testing drug susceptibility of a microorganism, comprising adding and reacting, in a liquid culture medium, an alkaline sensitizing solution and a coloring reagent comprising a redox dye, the liquid culture medium comprising an antimicrobial drug and having been inoculated with a test sample, thereby determining a minimum inhibitory concentration by coloration in the reaction.

Furthermore, the present invention relates to the above-mentioned test method wherein the microorganism is a yeast-like fungus and/or a filamentous fungus.

Moreover, the present invention relates to the above-mentioned test method wherein the liquid culture medium comprises a non-reducing sugar.

Furthermore, the present invention relates to a kit for testing drug susceptibility of a microorganism wherein the above-mentioned detection kit further comprises an antimicrobial drug.

Moreover, the present invention relates to the above-mentioned test kit wherein the antimicrobial drug is an antifungal drug.

In the method of the present invention, since a component that exhibits a color by reacting with an alkaline sensitizing solution is used as a coloring reagent, the color reaction in a detection operation after culturing a microorganism can be effected with extreme sensitivity. The coloration at this stage can be identified visually or by a normal absorptiometer. Furthermore, by selecting as a coloring reagent component a redox dye and, in particular, a water-soluble redox dye, the need for addition of an organic solvent and stirring after the color reaction is eliminated. In accordance with the method of the present invention, therefore, detection of a microorganism is extremely simple and precise.

In addition, the kit for detecting a microorganism and the drug susceptibility test kit of the present invention are portable. The kits of the present invention can therefore accomplish their respective objects without limiting the location where they are used.

DETAILED DESCRIPTION OF THE PREFERRED EMBODIMENTS

Figure 1:
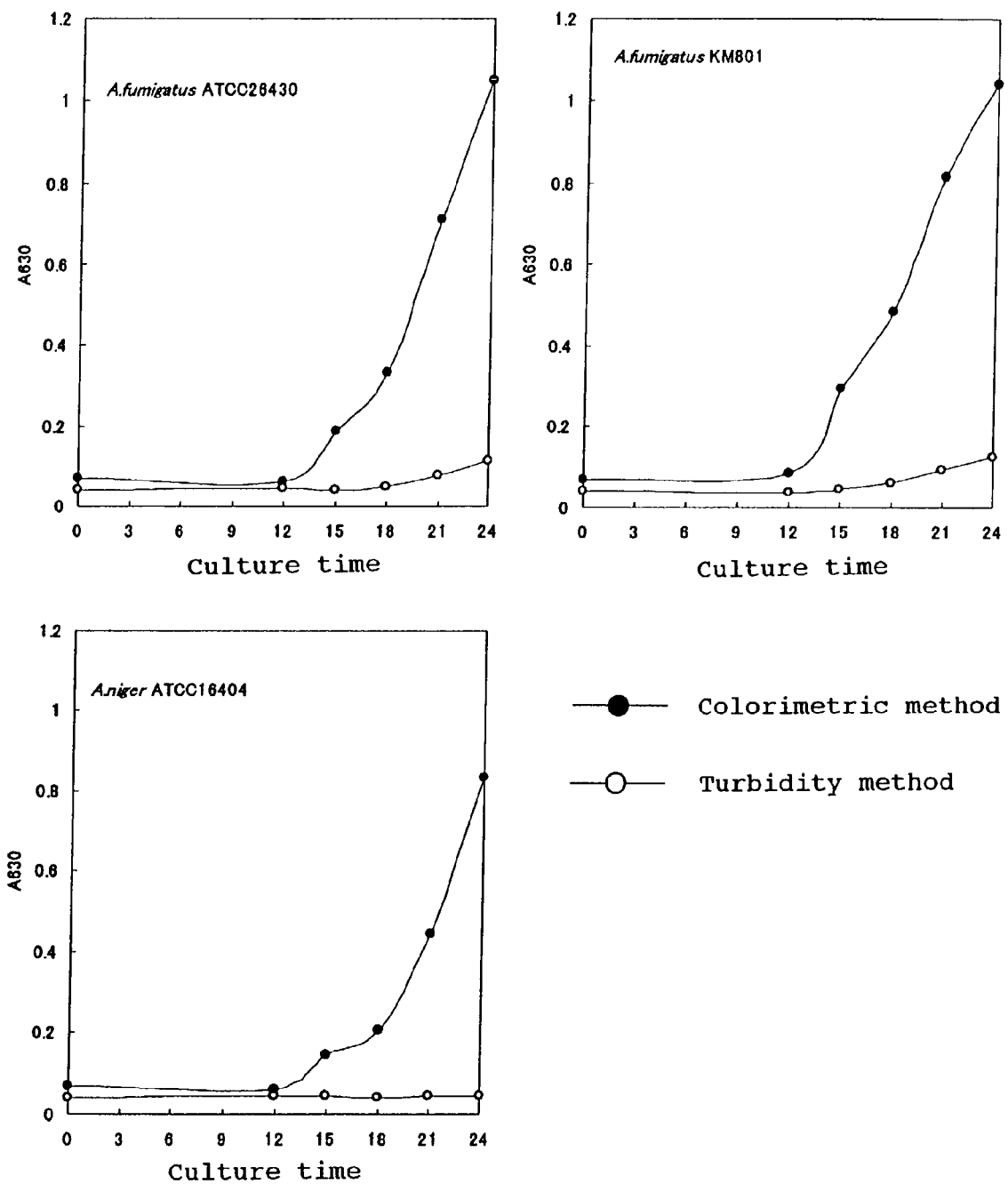
FIG. 1 is a graph showing the change in absorbance relative to culture time in the turbidity method, and in the colorimetry method of the present invention.

The carbon source that is used in the culture medium of the present invention is a sugar that does not show reducibility in neutral and alkaline solutions so as to avoid a blank reaction, and the metabolic product that is produced by the action of an enzyme produced by a microorganism that is to be detected shows reducibility in neutral and alkaline solutions. Examples thereof include sucrose, sorbitol, and trehalose. In the case where the filamentous fungus that is to be detected belongs to the genus *Aspergillus* or the genus *Penicillium*, since these fungi have invertase and produce a reducing sugar, it is preferable to use sucrose.

With regard to other nutrient sources, yeast extract, peptone, Yeast Nitrogen Base (manufactured by Difco), etc. can be cited. In the case where the object is to detect only a yeast-like fungus or a filamentous fungus, addition of an antibiotic such as chloramphenicol in order to suppress the growth of bacteria can also be considered.

Any coloring reagent may be used in the present invention as long as it exhibits a color under alkaline conditions, but one containing a redox dye and, in particular, a water-soluble redox dye, is preferably used. More specifically, a tetrazolium salt such as WST-1, WST-3, WST-4, WST-5 or WST-8 that forms a water-soluble formazan is preferred. In particular, WST-8 is preferably used.

With regard to other components that are contained in the coloring reagent, there can be cited an electron carrier having the function of donating an electron to the coloring reagent, and potassium ferricyanide and potassium ferrocyanide for adjusting the redox potential of the culture medium. As for the electron carriers, PMS (phenazine methosulfate), Meldola's Blue, diaphorase, 1-methoxy PMS, etc. are preferably used, and 1-methoxy PMS is particularly preferably used.

With regard to a component of the alkaline sensitizing solution used in the present invention, any component that makes the pH of the cultured liquid about 9 or above can be used, and since WST-8 formazan exhibits a blue color when the pH is about 9 or above, a component that makes the pH about 9 or above is suitably used, and one that makes the pH 10 or above is particularly preferred. Examples of preferably used components include sodium hydroxide and potassium hydroxide. Sodium hydroxide is preferable thereamong in terms of the change in the amount of liquid and the ease of addition. In this case, it is preferable to add a 1 to 2 mol/l aqueous solution of sodium hydroxide in an amount of $\frac{1}{20}$ to $\frac{1}{10}$ of the amount of cultured liquid.

Microorganisms to which the detection method of the present invention can be applied are not limited as long as they can grow in the above type of culture medium. In particular, filamentous fungi such as those of the genus *Aspergillus* and the genus *Penicillium* can be suitably detected.

Antimicrobial drugs that are used in the drug susceptibility test of the present invention are not limited as long as they are used for the treatment of an infection where the causative agent is a fungus, and examples thereof include Amphotericin B, Flucytosine, Fluconazole, Miconazole, Itraconazole, and Ketoconazole.

The kit for detecting a microorganism used in the present invention comprises a coloring reagent, a liquid culture medium, and an alkaline sensitizing solution, and the coloring reagent and the liquid culture medium may be mixed in advance.

The drug susceptibility test kit in the present invention comprises a coloring reagent, a liquid culture medium, an alkaline sensitizing solution, and an antimicrobial drug, and the coloring reagent, the liquid culture medium, and the antimicrobial drug may be mixed in advance.

In order to implement the present invention, after the coloring reagent is added to the culture medium, the culture medium is inoculated with a test sample and cultured. Alternatively, after inoculating the culture medium with a test sample and culturing, the coloring reagent is added thereto. Although the culturing conditions depend on the type of fungus that is to be detected, culturing is carried out, for example, at 35° C. to 37° C. for 24 to 48 hours. After culturing, the alkaline sensitizing solution is added, and the color of the liquid culture after 5 to 10 minutes is observed visually or measured using an absorptiometer. The wavelength used for this measurement is 620 to 660 nm. It is preferable to prepare a negative control which has not been inoculated with a test sample.

When implementing the drug susceptibility test using the method of the present invention, the coloring reagent, the liquid culture medium, and an antifungal drug such as Amphotericin B, Flucytosine, Fluconazole, Miconazole, Itraconazole, or Ketoconazole are pipetted into a microplate or a test tube, it is inoculated with a test microorganism, and the test microorganism is cultured. After culturing, the alkaline sensitizing solution is added thereto, and the minimum inhibitory concentration is determined by observing the color of the liquid culture visually or by absorbance. Alternatively, after inoculating a microplate or test tube, into which the above-mentioned antifungal drug and the liquid culture medium have been pipetted, with a test microorganism and culturing the test microorganism, the coloring reagent and then the alkaline sensitizing solution are added thereto, and the minimum inhibitory concentration is determined by observing the color of the liquid culture visually or by absorbance.

EXAMPLES

The present invention is explained in further detail below by reference to examples, but the present invention is in no way limited by these examples.

Example 1

In order to select a growth culture medium the following procedures were carried out.

A. Strain Used

*Aspergillus Fumigatus* KM8001 was used.

B. Test Method (1) Preparation of Culture Medium

1) MOPS Buffered RPMI 1640 Culture Medium Supplemented with Added Glucose 10.4 g of RPMI 1640 culture medium powder (containing L-glutamine, no sodium hydrogen carbonate, and no Phenol Red, manufactured by Gibco), 2.0 g of sodium hydrogen carbonate, 10.0 g of glucose, and 34.53 g of 3-morpholinopropanesulfonic acid (MOPS) were dissolved in 900 mL of purified water, and the pH was adjusted to 7.0 with a 1N aqueous solution of sodium hydroxide. The solution was made up to 1000 mL and then filtered using a 0.2 μm filter.

2) Preparation of Glucose YN Broth 6.7 g of YN Base (manufactured by Difco) and 5 g of glucose were dissolved in about 900 mL of purified water, and the pH was adjusted to 5.3 with a 1N aqueous solution of sodium hydroxide. The solution was made up to 1000 mL with purified water and then filter sterilized using a 0.2 μm filter.

3) Preparation of Sucrose YN Broth 6.7 g of YN Base (manufactured by Difco) and 20 g of sucrose were dissolved in about 900 mL of purified water, and the pH was adjusted to 7.0 with a 1N aqueous solution of sodium hydroxide. The solution was made up to 1000 mL with purified water and then filter sterilized using a 0.2 μm filter.

(2) Preparation of Inoculum and Culturing

A tester strain was cultured using Sabouraud Dextrose Agar (manufactured by OXOID) at 35° C. for 7 days. 2 mL of sterile physiological saline containing 0.1% Tween 80 was added dropwise onto the culture medium so as to float spores. The above-mentioned physiological saline that had been added dropwise onto the culture medium was recovered and allowed to stand for 3 to 5 minutes, and after removing the precipitate it was mixed using a Vortex mixer to give a spore suspension. Dilution was carried out so that the absorbance at 530 nm was 0.09 to 0.11. The spore suspension so prepared was diluted 100 times with various test culture media, 0.2 mL of each was pipetted into a well of a microplate, and 0.02 mL of a coloring reagent (containing 0.7 mmol/L WST-8, 0.0035 mmol/L 1-methoxy PMS, 0.5 mmol/L potassium ferricyanide, and 0.5 mmol/L of potassium ferrocyanide) was added thereto. As negative controls, various test culture media which had not been inoculated with a spore liquid (uninoculated with microorganisms) were prepared. Culturing was carried out at 35° C.±1° C. for 24 hours, and the absorbance at a primary wavelength of 450 nm and a secondary wavelength of 630 nm was measured. Subsequently, 0.02 mL of a 1.5 mol/L aqueous solution of sodium hydroxide was added to each of the wells, and 5 minutes after that the absorbance at 630 nm was measured.

C. Results

The results obtained by measuring the absorbance of each growth culture medium before and after addition of the aqueous solution of sodium hydroxide are summarized in Table 1. When the absorbance was measured at the primary wavelength of 450 nm and the secondary wavelength of 630 nm using the MOPS buffered RPMI 1640 culture medium supplemented with glucose, the absorbance was 0.153, which was considerably low. When the aqueous solution of sodium hydroxide was therefore added thereto in order to increase the sensitivity, and the absorbance at 630 nm was measured, a color was also observed for the uninoculated samples. The absorbance was then measured at 630 nm for the glucose YN broth and the sucrose YN broth before and after addition of the aqueous solution of sodium hydroxide. It was found that a color was exhibited for the uninoculated sample with the glucose YN broth. On the other hand, almost no coloration was observed for the uninoculated sample with the sucrose YN broth, but when the microorganisms grew they exhibited a strong color.

The present invention can therefore be carried out using a liquid culture medium containing sucrose.

(2) Preparation of Inoculum and Culturing

A tester strain was cultured using Sabouraud Dextrose Agar (manufactured by OXOID) at 35° C. for 7 days. 2 mL of sterile physiological saline containing 0.1% Tween 80 was added dropwise onto the culture medium so as to float spores. The above-mentioned physiological saline that had been added dropwise onto the culture medium was recovered and allowed to stand for 3 to 5 minutes, and after removing the precipitate it was mixed using a Vortex mixer to give a spore suspension. Dilution was carried out so that the absorbance at 530 nm was 0.09 to 0.11. 0.1 mL of the spore suspension so prepared was taken using a micro pipette, added to 10 mL of the sucrose YN broth containing 0.1 mg/mL of chloramphenicol, and stirred well using a Vortex mixer to give an inoculum.

(3) Turbidity Method 0.2 mL of the inocula prepared in (2) was pipetted into each well of a microplate. After covering the plate, it was cultured at 35° C.±1° C. The absorbance at 630 nm was measured at predetermined intervals.

(4) Colorimetry (Method of the Present Invention)

0.02 mL of a coloring reagent (containing 0.7 mmol/L WST-8, 0.0035 mmol/L 1-methoxy PMS, 0.5 mmol/L potassium ferricyanide, and 0.5 mmol/L of potassium ferrocyanide) and 0.2 mL of the inoculum prepared in (2) were pipetted into each well of a microplate. After the plate was

TABLE 1

Table 1 Absorbance before and after addition of aqueous solution of sodium hydroxide for various culture media

|  | Addition of aqueous solution of sodium hydroxide | Measurement wavelength | MOPS buffered RPMI 1640 culture medium supplemented with glucose | Glucose YN broth | Sucrose YN Broth |
| --- | --- | --- | --- | --- | --- |
| Uninoculated with Microorganisms | Before | 630 nm | 0.045 | 0.015 | 0.013 |
|  | After | 630 nm | 0.976 | 0.968 | 0.089 |
| Inoculated with microorganisms | Before | Primary wavelength 450 nm Secondary wavelength 630 nm | 0.153 | 0.024 | 0.017 |
|  | Before | 630 nm | 0.206 | 0.132 | 0.262 |
|  | After | 630 nm | 0.836 | 0.827 | 0.767 |

Example 2

In order to measure the degree of proliferation of a filamentous fungus the following procedures were carried out.

A. Strains Used

*Aspergillus Fumigatus* ATCC26430, *Aspergillus Fumigatus* KM8001, and *Aspergillus niger* ATCC16404 were used.

B. Test Method (1) Preparation of Sucrose YN Broth 6.7 g of YN Base (manufactured by Difco) and 20 g of sucrose were dissolved in about 900 mL of purified water, and the pH was adjusted to 7.0 with a 1N aqueous solution of sodium hydroxide. The solution was made up to 1000 mL with purified water and then filter sterilized using a 0.2 μm filter.

covered, it was cultured at 35° C.±1° C. After culturing for 12 hours, 0.02 mL of a 1.2 mol/L aqueous solution of sodium hydroxide was added in sequence every 3 hours to the wells that were being cultured, and 10 minutes after the addition the absorbance at 630 nm was measured. As a blank, sucrose YN culture medium was added instead of the inoculum.

C. Results

FIG. 1 shows the absorbance measured after culturing for 12, 15, 18, 21, and 24 hours. The ordinate of FIG. 1 denotes the absorbance at 630 nm, and the abscissa denotes the culture time. In the present invention, the absorbance increased with the culture time, and it was possible to measure the degree of proliferation. Furthermore, a color was exhibited after 18 hours when the turbidity had hardly changed, and detection in a short time was thus possible.

It therefore becomes clear that the measurement kit and the measurement method of the present invention allow the degree of proliferation of a filamentous fungus to be measured simply.

Example 3

In order to examine the applicability to antifungal drug susceptibility testing the following procedures were carried out.

A. Strain Used

*Aspergillus Fumigatus* ATCC26430 was used.

B. Microplate Used for Test

Two drugs, Amphotericin B (AMPH) and Itraconazole (ITCZ) were examined. 2-fold dilution series of AMPH (0.3 to 160 μg/mL) and ITCZ (0.16 to 80 μg/mL) were prepared using dimethyl sulfoxide and purified water. The drug solutions so prepared were pipetted into a plate at 0.02 mL/well and dried to a solid under reduced pressure for 24 hours. A coloring reagent (containing 0.7 mmol/L WST-8, 0.0035 mmol/L 1-methoxy PMS, 0.5 mmol/L potassium ferricyanide, and 0.5 mmol/L of potassium ferrocyanide) was pipetted into each of the wells at 0.02 mL/well and they were again dried to a solid under reduced pressure for 24 hours.

C. Test Method (1) Turbidity Method

A comparative example was carried out according to NCCLS M-38P (0.2 mL culture system micro broth dilution method).

(2) Microplate Method of the Present Invention

1) Preparation of Sucrose YN Broth 6.7 g of YN Base (manufactured by Difco) and 20 g of sucrose were dissolved in about 900 mL of purified water, and the pH was adjusted to 7.0 with a 1N aqueous solution of sodium hydroxide. The solution was made up to 1000 mL with purified water and then filter sterilized using a 0.2 μm filter.

2) Preparation of Inoculum and Culturing

A tester strain was cultured using Sabouraud Dextrose Agar (manufactured by OXOID) at 35° C. for 7 days. 2 mL of sterile physiological saline containing 0.1% Tween 80 was added dropwise onto the culture medium so as to float spores. The above-mentioned physiological saline that had been added dropwise onto the culture medium was recovered and allowed to stand for 3 to 5 minutes, and after removing the precipitate it was mixed using a Vortex mixer to give a spore suspension. Dilution was carried out so that the absorbance at 530 nm was 0.09 to 0.11. 0.1 mL of the spore suspension so prepared was taken using a micro pipette, added to 20 mL of sucrose YN broth, and stirred using a Vortex mixer to give an inoculum. 0.2 mL of the inoculum was pipetted into each of the wells of the microplate for the test described in B, the plate was covered, and culturing was carried out at 35° C.±1° C. for 24 hours. As a blank, sucrose YN broth was added instead of the inoculum.

3) Evaluation Method

After 24 hours 0.02 mL of a 1.5 mol/L aqueous solution of sodium hydroxide was added to each well, and 5 minutes after the addition the absorbance at 630 nm was measured.

1. For AMPH, the minimum concentration that gave an absorbance equal to or less than that of the negative control was defined as the minimum inhibitory concentration (MIC).

2. For ITCZ, the 80% inhibitory concentration (IC80) was determined. The drug concentration of a well that gave an absorbance equal to or less than that obtained by the following equation was defined as the MIC.

(IC80=(positive control−negative control)×0.2+negative control)

D. Results

Figure 2:
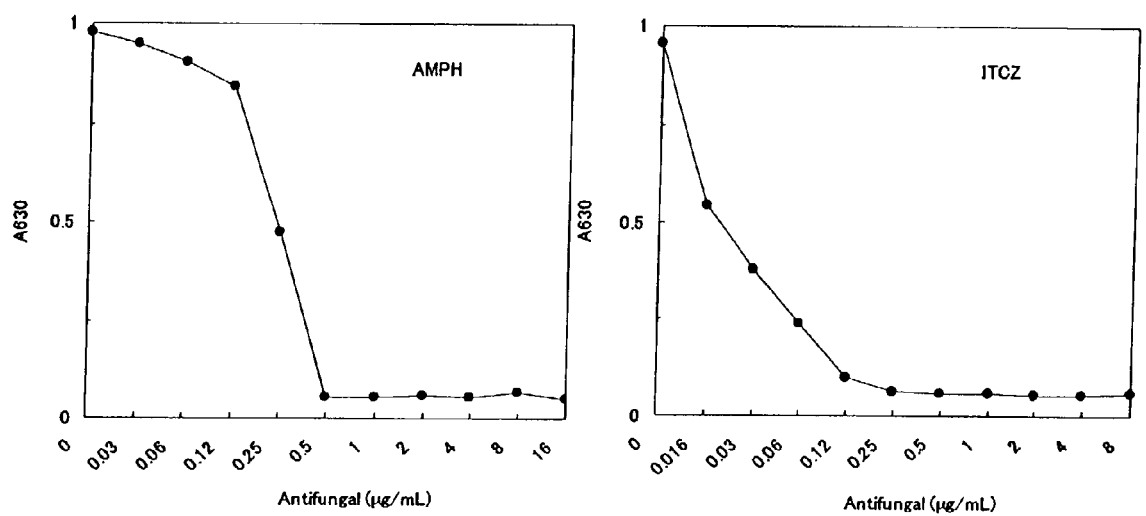
FIG. 2 is a graph showing the change in absorbance relative to antifungal drug concentration when carrying out a drug susceptibility test for *A. fumigatus* ATCC26430.

FIG. 2 shows the results of measuring the absorbance when evaluating the drug susceptibility in accordance with the present invention. The abscissa denotes the antifungal drug concentration, and the ordinate denotes the absorbance at 630 nm. The absorbance increased when the concentration became 0.25 μg/mL or below for AMPH and 0.06 μg/mL or below for ITCZ. Visually, AMPH exhibited a blue to dark blue color at 0.25 μg/mL or below and almost no color at 0.5 μg/mL or above, and ITCZ exhibited a blue to dark blue color at 0.06 μg/mL or below and almost no color at 0.12 μg/mL or above. The drug susceptibility test was carried out repeatedly by the NCCLS M-38P method and the method of the present invention, and the MIC values obtained thereby are summarized in Table 2. In the table, the allowable range denotes the reference values described in NCCLS M38-P. It was found that the MIC determined in the present invention coincided with the allowance range described in NCCLS M38-P. Furthermore, the MIC values determined visually were the same as those determined using absorbance. Moreover, the time for determination with the NCCLS M38-P method was 46 to 50 hours, but the present invention took about half of the above, that is, 24 hours.

The measurement reagent and the measurement method of the present invention are therefore useful for testing the antifungal drug susceptibility of a filamentous fungus.

TABLE 2

| | MIC (units μg/mL) of *A. fumigatus* ATCC 26430 | | |
|---|---|---|---|
| | Measurement method | MIC | Allowable range |
| AMPH | M-38P (Turbidity method) | 0.5–2.0 | 0.5–2.0 |
| | Colorimetry | 0.5–1.0 | |
| ITCZ | M-38P (Turbidity method) | 0.12–0.25 | 0.12–1.0 |
| | Colorimetry | 0.12–0.25 | |

Effects of the Invention

In accordance with the detection method and the detection kit of the present invention, microorganisms and, in particular, yeast-like fungi and filamentous fungi can be easily detected. Furthermore, the drug susceptibility test method and the kit therefor of the present invention are useful for testing the antifungal drug susceptibility of a filamentous fungus by a broth dilution method.

What is claimed is:

1. A method for detecting a viable microorganism, comprising:

adding and reacting, in a liquid culture medium, an alkaline sensitizing solution, a non-reducing sugar and a coloring reagent comprising a redox dye, potassium ferricyanide and potassium ferrocyanide, the liquid culture medium having been inoculated with a test sample suspected of containing a microorganism, thereby detecting the microorganism by coloration in the reaction.

2. The method according to claim 1 wherein the microorganism is a yeast-like fungus and/or a filamentous fungus.

3. A kit for detecting a microorganism comprising:
a coloring reagent comprising a redox dye, potassium ferricyanide and potassium ferrocyanide;
a liquid culture medium;
a non-reducing sugar; and
an alkaline sensitizing solution.

4. The kit according to claim 3 wherein the redox dye is a water-soluble tetrazolium salt that forms a water-soluble formazan.

5. The kit according to claim 4 wherein the tetrazolium salt that forms the water-soluble formazan is 2-(2-methoxy-4-nitrophenyl)-3-(4-nitrophenyl)-5-(2,4-disulfophenyl)-2H-tetrazolium, sodium salt.

6. The kit according to claim 3 wherein the coloring reagent further comprises an electron carrier.

7. The kit according to claim 6 wherein the electron carrier is 1-methoxy-5-methyiphenazinium methylsulfate.

8. The kit according to claim 3 wherein the non-reducing sugar is sucrose.

9. The kit according to claim 3 wherein the alkaline sensitizing solution is one that makes the pH of the liquid culture medium at least 9.

10. The kit according to claim 3 wherein the alkaline sensitizing solution is an aqueous solution of sodium hydroxide.

11. A method for testing drug susceptibility of a microorganism, comprising:
adding and reacting, in a liquid culture medium, an alkaline sensitizing solution, a non-reducing sugar, and a coloring reagent comprising a redox dye, potassium ferricyanide and potassium ferrocyanide, the liquid culture medium comprising an antimicrobial drug and having been inoculated with a test sample containing a microorganism, thereby determining a minimum inhibitory concentration by coloration in the reaction.

12. The method according to claim 11 wherein the microorganism is a yeast-like fungus and/or a filamentous fungus.

13. A kit for testing drug susceptibility of a microorganism wherein the detection kit according to claim 3 further comprises an antimicrobial drug.

14. The kit according to claim 13 wherein the antimicrobial drug is an antifungal drug.

15. The method according to claim 1 wherein the coloring reagent further comprises an electron carrier.

16. The method according to claim 15 wherein the electron carrier is 1-methoxy-5-methylphenazinium methylsulfate.

17. The method according to claim 1 wherein the non-reducing sugar is sucrose.

18. The method according to claim 1 wherein the redox dye is a water-soluble tetrazolium salt that forms a water-soluble formazan.

19. The method according to claim 18 wherein the tetrazolium salt that forms the water-soluble formazan is 2-(2-methoxy-4-nitrophenyl)-3-(4-nitrophenyl)-5-(2,4-disulfophenyl)-2H-tetrazolium, sodium salt.

20. The method according to claim 1 wherein the alkaline sensitizing solution is one that makes the pH of the liquid culture medium at least 9.

21. The method according to claim 20 wherein the alkaline sensitizing solution is an aqueous solution of sodium hydroxide.

22. The method according to claim 11 wherein the coloring reagent further comprises an electron carrier.

23. The method according to claim 22 wherein the electron carrier is 1-methoxy-5-methylphenazinium methylsulfate.

24. The method according to claim 11 wherein the non-reducing sugar is sucrose.

25. The method according to claim 11 wherein the redox dye is a water-soluble tetrazolium salt that forms a water-soluble formazan.

26. The method according to claim 25 wherein the tetrazolium salt that forms the water-soluble formazan is 2-(2-methoxy-4-nitrophenyl)-3-(4-nitrophenyl)-5-(2,4-disulfophenyl)-2H-tetrazolium, sodium salt.

27. The method according to claim 11 wherein the alkaline sensitizing solution is one that makes the pH of the liquid culture medium at least 9.

28. The method according to claim 27 wherein the alkaline sensitizing solution is an aqueous solution of sodium hydroxide.

29. The method according to claim 20, wherein the redox dye is 2-(2-methoxy-4-nitrophenyl)-3 -(4-nitrophenyl)-5-(2,4-disulfophenyl)-2H-tetrazolium, sodium salt.

30. The method according to claim 27, wherein the redox dye is 2-(2-methoxy-4-nitrophenyl)-3-(4-nitrophenyl)-5-(2,4-disulfophenyl)-2H-tetrazolium, sodium salt.

31. The kit according to claim 5, wherein the alkaline sensitizing solution makes the pH of the medium at least 9.

* * * * *